(12) United States Patent
Lubitz et al.

(10) Patent No.: US 7,332,323 B2
(45) Date of Patent: Feb. 19, 2008

(54) **STRAIN OF *SPHINGOMONAS PITUITOSA* AND METHOD OF EXOPOLYSACCHARIDE PRODUCTION THEREFROM**

(75) Inventors: Werner Lubitz, Schönborngasse 12/7, 1080 Wien, Österreich (AT); Ewald B. M. Denner, Vienna (AT)

(73) Assignee: Werner Lubitz, Klosterneuburg/Kritzendorf (AT)

( * ) Notice: Subject to any disclaimer, the term of this patent is extended or adjusted under 35 U.S.C. 154(b) by 554 days.

(21) Appl. No.: 10/475,880

(22) PCT Filed: Apr. 23, 2002

(86) PCT No.: PCT/EP02/04464

§ 371 (c)(1),
(2), (4) Date: Oct. 24, 2003

(87) PCT Pub. No.: WO02/086099

PCT Pub. Date: Oct. 31, 2002

(65) Prior Publication Data

US 2004/0197877 A1    Oct. 7, 2004

(30) Foreign Application Priority Data

Apr. 24, 2001  (DE) ................. 101 20 061

(51) Int. Cl.
*C12N 1/20* (2006.01)
(52) U.S. Cl. .............. 435/252.3; 435/101; 514/54
(58) Field of Classification Search ............ 435/101, 435/252.1; 536/123, 123.1; 514/54; 426/658
See application file for complete search history.

(56) References Cited

U.S. PATENT DOCUMENTS 5,338,681 A * 8/1994 Deckwer et al. ......... 435/252.1
5,854,034 A   12/1998 Pollock et al.

FOREIGN PATENT DOCUMENTS

EP      0 507 234 A    10/1992

OTHER PUBLICATIONS

Kämpfer et al (Int. J. Syst. Bacteriol. 47(2):577-583 (1997)).*
Denner E. B. M. et al., "*Sphingomonas pituitosa* sp. nov., an Exopolysaccharide-Producing Bacterium That Secretes and Unusual Type of Sphingan" *International Journal of Systematic and Evolutionary Microbiology*, 2001, vol. 51, No. 3, pp. 827-841, XP-008016073.
Anson A. et al., "A Bacterium Yielding a Polysaccharide with Unusual Properties" *Journal of Applied Bacteriology*, Oxford, GB, 1987, vol. 62, No. 2, pp. 147-150, XP-000121053.
Lobas D. et al., "Structure and Physical Properties of the Extracellular Polysaccharide PS-P4 Produced by *Sphingomonas paucimobilis* P4 (DSM 6418)" *Carbohydrate Research*. Netherlands, 1994, vol. 251, pp. 303-313, XP-001148893.
Moore E. R. B. et al., "*Sphingomonas pituitosa* Partial 16S rRNA Gene, Strain EDIV" Retrieved from EBI, Database Accession No. AJ243751, 2000, XP-002238096 (abstract).
Pollock T. J., "Gellan-Related Polysaccharides and the Genus *Sphingomonas*" *Journal of General Microbiology, Society for Microbiology*, Reading, GB, 1993, vol. 139, No. Part 8, pp. 1939-1945, XP-002035685.

* cited by examiner

*Primary Examiner*—Sandra E. Saucier
*Assistant Examiner*—Aaron J. Kosar
(74) *Attorney, Agent, or Firm*—Rothwell, Figg, Ernst & Manbeck, P.C.

(57) ABSTRACT

The present invention concerns a new epoxypolysaccharide-producing bacterium, the exopolysaccharide isolated from this bacterium and the use of the exopolysaccharide.

6 Claims, 1 Drawing Sheet

Fig 1:
SEQ ID NO:1

```
   1 aacgaacgct ggcggcatgc ctaacacatg caagtcgaac gagatccttc ggggtctagt
  61 ggcgcacggg tgcgtaacgc gtgggaatct gcctcggggt tcggaataac tccccgaaag
 121 gggtgctaat accggatgat gtcgaaagac caaagattta tcgccctgag atgagcccgc
 181 gtaggattag ctagttggtg tggtaaaggc gcaccaaggc gacgatcctt agctggtctg
 241 agaggatgat cagccacact gggactgaga cacggcccag actcctacgg gaggcagcag
 301 tggggaatat tggacaatgg gcgaaagcct gatccagcaa tgccgcgtga gtgatgaagg
 361 ccttagggtt gtaaagctct tttacccggg aagataatga ctgtaccggg agaataagcc
 421 ccggctaact ccgtgccagc agccgcggta atacggaggg ggctagcgtt gttcggaatt
 481 actgggcgta aagcgcacgt aggcggcttt gtaagtcaga ggtgaaagcc tggagctcaa
 541 ctccagaact gcctttgaga ctgcatcgct tgaatccagg agaggtgagt ggaattccga
 601 gtgtagaggt gaaattcgta gatatcgga agaacaccag tggcgaaggc ggctcactgg
 661 actggtattg acgctgaggt gcgaaagcgt ggggagcaaa caggattaga taccctggta
 721 gtccacgccg taaacgatga taactagctg tccgggcact tggtgcttgg gtggcgcagc
 781 taacgcatta agttatccgc ctggggagta cggccgcaag gttaaaactc aaaggaattg
 841 acgggggcct gcacaagcgg tggagcatgt ggtttaattc gaagcaacgc gcagaacctt
 901 accagcgttt gacatggtag gacgacttcc agagatggat ttcttccctt cggggaccta
 961 cacacaggtg ctgcatggct gtcgtcagct cgtgtcgtga gatgttgggt taagtcccgc
1021 aacgagcgca accctcgact ttagttacca tcattaagtt gggtacttta aagtaaccgc
1081 cggtgataag ccggaggaag gtggggatga cgtcaagtcc tcatggccct tacgcgctgg
1141 gctacacacg tgctacaatg gcaagtacag tgggcagcaa tcccgcgagg gtgagctaat
1201 ctccaaaact tgtctcagtt cggattgttc tctgcaactc gagagcatga aggcggaatc
1261 gctagtaatc gcggatcagc atgccgcggt gaatacgttc ccaggccttg tacacaccgc
1321 ccgtcacacc atgggagttg gttcacccg aaggcgttgc gctaactcag caatgagagg
1381 caggcgacca cggtgggctt agcgactggg gtgaagtcgt aacaaggtag ccgtagggga
1441 acctgc
```

STRAIN OF *SPHINGOMONAS PITUITOSA* AND METHOD OF EXOPOLYSACCHARIDE PRODUCTION THEREFROM

CROSS REFERENCE TO RELATED APPLICATION

This application is a 35 USC § 371 National Phase Entry Application from PCT/EP02/04464, filed Apr. 23, 2002, and designating the U.S.

The present invention concerns a new exopolysaccharide-producing bacterium, the exopolysaccharide (referred to as PS-EDIV) isolated from this bacterium and the use of the exopolysaccharide.

The genus *Sphingomonas* is a taxon that has been continually expanding since its description by Yabuuchi et al. (1990) (Takeuchi et al., 1993, 1995; Nohynek et al., 1996; Zipper et al., 1996; Balkwill et al., 1997; Kämpfer et al., 1997; Denner et al., 1999). There is much interest in sphingomonads since they have a wide range of catabolic abilities and thus have great potential for biotechnological applications. For example sphingomonads can be used to degrade xenobiotic compounds in waste water treatment, as bacterial antagonists for phytopathogenic fungi and they can also be used to produce industrially utilizable exopolysaccharides (Pollock, 1993).

Hence the object of the present invention was to provide a new microorganism of the genus *Sphingomonas* that can be used for biotechnological applications or/and to produce industrially utilizable products.

This object is achieved according to the invention by a new exopolysaccharide-producing bacterium which is referred to herein as $EDIV^T$ or as *Sphingomonas pituitosa* sp. nov. and has been deposited at the DSMZ "Deutsche Sammlung von Mikroorganismen und Zellkulturer GmbH", Mascheroder Weg 1b, 38124 Braunschweig under the accession number DSM 13101 or DSM 14559 and at the Collection de l'Institut Pasteur-CIP, B.P. 52, 25, rue de Dr. Roux, 75724 Paris Cedex, France under the accession number CIP 106154T. The new bacterial strain according to the invention is able to produce a highly viscous extracellular polysaccharide in a mineral medium containing sucrose.

The microorganism according to the invention can for example be stored at −70° C. in tryptic soy broth (Oxoid) which contains 15% glycerol. The strain $EDIV^T$ according to the invention is a gram-negative, oxidase-negative and catalase-positive, aerobic, non-spore-forming, motile rod-shaped bacterium having a respiratory metabolism. It produces a yellow intracellular pigment (carotenoids) which is not fluorescent and cannot diffuse out of the organism. Colonies of the microorganism are yellow, circular, lowly convex and smooth. The oxidase reaction is negative and the catalase reaction is positive. Positive reactions were obtained for the β-galactosidase test. Negative reactions were obtained for nitrate reduction, the urease test, production of indol and for arginine dihydrolase, gelatin liquefaction, $H_2S$ production and citrate utilization.

The following compounds are assimilated by the new organism: N-acetyl-D-glucosamine, L-arabinose, p-arbutin, D-cellobiose, D-galactose, D-glucose, D-mannose, D-maltose α-D-melibiose, sucrose, salicin, D-trehalose, D-xylose, acetate, fumarate, DL-3-hydroxybutyrate, L-malate, pyruvate, L-alanine and L-proline.

The following compounds are not assimilated by the organism according to the invention: D-fructose, gluconate, L-rhamnose, D-ribose, adonitol, i-inositol, maltitol, D-mannitol, D-sorbitol, putrescine, propionate, cis-aconitate, trans-aconitate, adipate, 4-aminobutyrate, azelate, citrate, glutarate, itaconate, DL-lactate, mesaconate, oxoglutarate, suberate, b-alanine, L-aspartate, L-histidine, L-leucine, L-ornithine, L-phenylalanine, L-serine, L-tryptophan, 3-hydroxybenzoate, 4-hydroxybenzoate and phenylacetate.

The following compounds are hydrolysed by the microorganism according to the invention: esculin, pNP-β-galactopyranoside, pNP-b-glucuronide, pNP-α-glucopyranoside, pNP-β-xylopyranoside, bis-pNP-phosphate, pNP-phenylphosphate, pNP-phosphorylcholine, 2-deoxythymidine-5'-pNP-phosphate, L-alanine-pNP and L-glutamate-γ-3-carboxy-pNA.

L-proline-pNA is not hydrolysed by the organism.

Ubiquinone Q-10 was found to be the main respiratory isoprenoid-quinone system of the new organism. Analysis of the polyamine content showed that symhomospermidine (68.4 µmol $g^{-1}$, dry weight) was the main compound and spermidine (3.3 µmol $g^{-1}$, dry weight) and spermine (1.0 µmol $g^{-1}$, dry weight) were minor components.

The main components of the polar lipids were phosphatidylethanolamine, phosphatidyldiethaolamine, phosphatidyldimethylethanolamine, phosphatidylglycerol, diphosphatidylglycerol and sphingoglycolipid.

The composition of the cellular fatty acids of the microorganism $EDIV^T$ is as follows: cis 18:1 (58.6%), 16:0 (20.9%) and 2-OH 14:0 (10.0%) as the main components of the fatty acids as well as smaller amounts of cis 16:1 and cis 17:0 c. It was also found that the G+C content of the DNA of the organism according to the invention is 64.5 mol % which is a value that is within the range found for members of the genus *Sphingomonas* (Yabuuchi et al., 1990).

Another subject matter of the present invention is the ribosomal rDNA of the strain $EDIV^T$. The 16S rDNA sequence to the strain $EDIV^T$ was determined and is shown in SEQ ID NO:1. A high degree of sequence similarity was observed between $EDIV^T$ and *Sphinomonas trueperi* (DSM 7225) with a similarity of 99.4%.

An analysis of the 16S rRNA gene sequence showed that the strain $EDIV^T$ can be classified within the α-4 subclass of proteobacteria.

Hence the invention also concerns the ribosomal DNA of the microorganism *Sphingomonas pituitosa* sp. nov. comprising (a) the nucleotide sequence shown in SEQ ID NO:1, (b) a sequence corresponding to the nucleotide sequence shown in SEQ ID NO:1 within the scope of the degeneracy of the genetic code or (c) a sequence which hybridizes with the sequences of (a) or/and (b) under stringent conditions.

The invention also encompasses sequences which hybridize under stringent conditions with the nucleotide sequence shown in SEQ ID NO:1 or with a sequence corresponding to this sequence within the scope of the degeneracy of the genetic code. The term "hybridization under stringent conditions" is used herein as in Sambrook et al. (Molecular Cloning, A Laboratory Manual, Cold Spring Harbor Laboratory Press (1989), 1.101-1.104). A stringent hybridization according to the invention is preferably present when a positive hybridization signal is observed after washing for 1 hour with 1×SSC and 0.1% SDS at 50° C., preferably at 55° C., more preferably at 62° C. and most preferably at 68° C. and more preferably for 1 hour with 0.2×SSC and 0.1% SDS (sodium dodecyl sulfate) at 50° C., preferably at 55° C., more preferably at 62° C. and most preferably at 68° C.

If the microorganism according to the invention is cultured on a medium which contains sucrose and in particular sucrose as the main carbon and energy source, large amounts of extracellular polysaccharide are formed. This polysaccharide is obtained especially in the form of an extracellular slime. Liquid cultures and colonies on agar media were highly viscous. Hence the invention also concerns a polysaccharide that can be produced by using the new exopolysaccharide-producing bacterium.

An analysis of the polysaccharide showed that it contains rhamnose and glucose units.

The polysaccharide or exopolysaccharide according to the invention can of course also be produced synthetically.

Furthermore the polysaccharide according to the invention has a molecular weight of >2500 kDa, more preferably of at least 2900 kDa and up to 3500 kDa, in particular up to 3100 kDa. The molecular weight is particularly preferably about 3000 kDa. The polysaccharide according to the invention has numerous advantageous properties which make it interesting for many applications. Hence it is pseudoplastic and thixotropic, it is resistant to boiling for 30 minutes and is extremely stable at temperatures between 25 and 99° C. and within wide pH ranges for example from pH 1 to pH 12.3. Furthermore it can be completely degraded after autoclave treatment. It is preferably produced by using $EDIV^T$ cells that are growing logarithmically and these cells are preferably cultured for 48 hours at 28° C. In order to obtain a high viscosity, the culture is preferably grown at a high rate of perturbation or/and a high oxygen concentration.

The polysaccharide according to the invention can be classified as a sphingan and is particularly suitable for applications in food technology e.g. as a gelatinizing agent or/and in pharmaceutical technology e.g. to formulate or encapsulate drugs. In particular a delayed release of the active substance can be obtained by coating or encapsulating active substances with the polysaccharide according to the invention.

The polysaccharide according to the invention can also be used advantageously in the chemical industry or/and in medicine. Numerous potential applications for example include its use as an adjuvant for tissue engineering, as a wound gel or as an excipient for drugs. It is also very suitable as a medium for paints and lacquers, as a carrier for adhesives or as a biopolymer for degradable plastics. Furthermore the polysaccharide according to the invention can also be used as a component of foods and especially for functional foods or novel food products.

FIG. 1 shows SEQ ID NO:1 which is the sequence of the 16S ribosomal RNA of *Sphingomonas pituitosa* sp. nov.

The invention is further elucidated by the following examples.

EXAMPLE 1

Production, yield and characterization of the exopolysaccharide (PS-EDIV) growth conditions and growth medium.

For the growth and exopolysaccharide investigations cells of $EDIV^T$ were cultured in a mineral salt medium which contained sucrose at a concentration of 3, 6, 9, 12, 15, 18, 20 or 22% (weight/vol) or glucose at a concentration of 12 or 15% (weight/vol). 100 ml of the following medium was inoculated with 100 µl of a cell suspension (in 0.85% NaCl solution) and incubated at 28° C. for up to 8 days in a water bath shaker. The rotation rate was adjusted to a higher level (500 to 800 rpm) when the medium became too viscous due to exopolysaccharide generation. Medium: pH 7.3 (±0.2), 1 g/l dipotassium hydrogen phosphate, 0.5 g/l KCl, 0.01 g/l $Fe(III)SO_4$, 0.5 g/l $MgSO_4$. 7 $H_2O$, 3 g/l $NaNO_3$, sucrose according to the desired concentrations stated above or glucose according to the desired concentrations stated above. In order to further extract EPS, sucrose was for example added at a concentration of 15% (weight/vol). $EDIV^T$ were incubated at 28° C.

A modified S medium as previously described (Fialho et al., 1991) without $K_2SO_4$ was also used to estimate the yield of EPS production after an incubation at 28° C. for 144 hours.

Extraction, deacetylation and hydrolysis of the exopolysaccharide

The exopolysaccharide was precipitated with a three-fold volume of 1-propanol as described by Azeredo and Olivera (1996). The highly viscous bacterial nutrient solution was firstly diluted (1:10) and centrifuged for 30 minutes at 9000 rpm, washed 3 times with propanol and lyophilized. The deacylation was carried out as described by Kang et al., (1982). The deacylated exopolysaccharide (EPS) was precipitated with a double volume of 1-propanol and dried by lyophilization. In order to analyse the composition, the native as well as the deacylated PS-EDIV was hydrolysed with trifluoroacetic acid as described by Hashimoto and Murata, 1998. The trifluoroacetic acid was completely evaporated under a vacuum at room temperature. The remaining hydrolysed PS-EDIV was taken up in HPLC water (Merck). The PS-EDIV samples can be stored frozen at −20° C.

The monosaccharides of the hydrolysed PS-EDIV were separated by thin layer chromatography on silica gel plates (silica gel $F_{254}$, Merck) using acetone/butanol/water (40:5:5, vol/vol) and butanol/acetic acid/water (4:6:1, vol/vol) as solvent systems. 1 to 2 µl of the PS-EDIV hydrolysate was applied to the thin layer plate.

Typical components for sphingans such as glucose, glucuronic acid, rhamnose and mannose were used as reference. The components were detected by heating the thin layer plates for 5 minutes at 110° C. after spraying with 10% (vol/vol) sulphuric acid in ethanol (Hashimoto and Murata, 1998) or α-naphthol.

In addition hydrolysates of PS-EDIV and the reference substances (glucose, rhamnose, mannose and glucuronic acid) were separated by HPLC using an Aminex HPX98-H column and 0.05 N $H_2SO_4$ as an eluant at an operating temperature of 60° C. and a flow rate of 0.5 ml/min.

It was found that the polysaccharide isolated from the strain $EDIV^T$ contains rhamnose and glucose.

LITERATURE REFERENCE

Auling, G., Busse, H. J., Pilz, F., Webb, L., Kneifel, H. & Claus, D. (1991), Int. J. Syst. Bacteriol 41: 223-228

Azerodo, J. & Olivera, R. (1996), Biotechnology Techniques 10: 341-344

Balkwill, D. L., Drake, G. R., Reeves, R. H., Frederikson, J. K., White, D. C., Ringelberg, D. B., Chandler, D. P., Romine, M. F., Kennedy, D. W. & Spandoni, C. M. (1997), Int. J. Syst. Bacteriol. 47: 191-201

Busse, J. & Auling G., (1988), Syst. Appl. Microbiol. 11: 1-8

Busse, H.-J., Bunka, S., Hensel, A. & Lubitz, W. (1997), Int. J. Syst. Bacteriol. 47: 698-708.

Crescenzi, V. (1995), Europe Biotechnol. Prog. 11: 251-259

Denner, E. B. M., Kämpfer, P., Busse, H.-J. & Moore, E. R. B. (1999), Int. J. Syst. Bacteriol. 49: 1103-1109

DeVos, P. & De Ley, J., (1983), Int. J. Syst. Bacteriol. 33: 487-509

DeVos, P., Van Landschoot, A., Segers, P., Tytgat, R., Gillis, M., Bauwens, M., Roussau, R., Goor, M., Pot, B., Kersters, K., Lizzaraga, P. & De Ley, J. (1989), Int. J. Syst. Bacteriol 39: 35-49

Hamana, K. & Matsuzaki, S. (1991), Can. J. Microbiol. 39: 304-310
Hashimoto, W. & Murato, K. (1998), Biosci. Biotechnol. Biochem. 62: 1068-1074
Jenkins, C. L., Andrews, A. G., McQuade, T. J. & Starr, M. P. (1979), Curr. Microbiol. 3: 1-4
Jukes, T. H. & Canto, C. R. (1969) In Mammalian Protein Metabolism, p. 21-132, Edited by Munro, H. N. New York, Academic Press
Kang, K. S., Veeder, G. T., Nirrasoul, P. J. Kaneto, T., & Cottrell, I. W. (1982) Agar-like polysaccharide produced by a Pseudomonas species: production and properties, Appl. Environ. Microbiol. 43, 1086-1091
Käümpfer, P. & Altwegg, M. (1992), J. Appl. Bacteriol. 72: 341-351
Kämpfer, P., Bark, K., Busse., H.-J., Auling, G. & Dott, W. (1992), Syst. Appl. Microbiol. 15: 309-419
Kämpfer, P. & Kroppenstedt, R. M. (1996), Can. J. Microbiol. 42: 989-1005
Kämpfer, P., Steiof, M. & Dott, W. (1991), Microbial. Ecol 21: 227-251
Kämpfer, P., Denner, E. B. M., Meyer, S., Moore, E. R. B. & Busse, H.-J. (1997), Int. J. Syst. Bacteriol 47: 577-583
Kroppenstedt, R. M. (1982), GIT Lab. Med. 5: 266-275
Moore, E. R. B., Wittich, R.-M., Fortnagel, P. & Timmis, K. N. (1993), Lett. Appl. Microbiol. 17: 115-118
Nohynek, L., Suhonen, E., Nurmiaho-Lassila, E.-L., Hantula, J. & Salkinoja-Salonen, M. (1996), Syst. Appl. Microbiol. 18: 527-538
Pollock, T. J. (1993), J. Gen. Microbiol. 139: 1939-1945
Scherer, F. & Kneifel, H. (1983), J. Bacteriol. 154: 1315-1322
Stackebrandt, E., Murray, R. G. E. & Trüper, H. G. (1988), Int. J. Syst. Bacteriol. 38: 321-325
Sutherland, I. W. (1982), Adv. Microb. Physiol. 33: 79-150
Sutherland, I. W. (1990), Camb. Stud. Biotechnol. 9: 1-151
Takeuchi, M., Kawai, F., Shimada, Y., & Yokota, A. (1993), Syst. Appl. Microbiol. 16: 227-238
Takeuchi, M., Sakane, T., Yanagi, M., Yamasato, K., Hamana, K. & Yokota, A. (1995), Int. J. Syst. Bacteriol. 45: 334-341
Takeuchi, M., Sawada, H., Oyaizu, H. & Yokota, A. (1994), Int. J. Syst. Bacteriol. 44: 308-314
Tindall, B. J. (1990), FEMS Microbiol. Lett 66: 199-202
Woese, C. R., Blanz, P. & Hahn, C. M. (1984), Syst. Appl. Microbiol. 5: 179-195
Woese, C. R. (1987), Microbiol. Rev 51: 221-271
Yabuuchi, E., Yano, T., Oyaizu, H., Hashimoto, Y., Ezaki, T. & Yamamoto, H. (1990), Microbiol. Immunol. 34: 99-119
Zipper, C., Nickel, K., Angst, W. & Kohler, H.-P. (1996), Appl. Environm. Microbiol. 62: 4318-4322.

The invention claimed is:

1. A biologically pure culture of microorganism *Sphingomonas pituitosa* sp. nov. DSM 14559.

2. A method for producing a polysaccharide comprising culturing the microorganism of claim 1 under conditions suitable to produce said polysaccharide.

3. The method according to claim 2, wherein said polysaccharide is extracellular.

4. The method according to claim 2 wherein said microorganism is cultured in a mineral medium containing sucrose.

5. The method according to claim 2 wherein said microorganism is cultured with perturbation.

6. The method according to claim 2, wherein said polysaccharide is a sphingan which contains rhamnose and glucose units.

* * * * *

```
                        SEQUENCE LISTING

<160> NUMBER OF SEQ ID NOS: 1

<210> SEQ ID NO 1
<211> LENGTH: 1446
<212> TYPE: DNA
<213> ORGANISM: Sphingomonas pituitosa

<400> SEQUENCE: 1
aacgaacgct ggcggcatgc ctaacacatg caagtcgaac gagatccttc ggggtctagt      60
ggcgcacggg tgcgtaacgc gtgggaatct gccttggggt tcggaataac tccccgaaag     120
gggtgctaat accggatgat gtcgaaagac caaagattta tcgccctgag atgagcccgc     180
gtaggattag ctagttggtg tggtaaaggc gcaccaaggc gacgatcctt agctggtctg     240
agaggatgat cagccacact gggactgaga cacggcccag actcctacgg gaggcagcag     300
tggggaatat tggacaatgg gcgaaagcct gatccagcaa tgccgcgtga gtgatgaagg     360
ccttagggtt gtaaagctct tttacccggg aagataatga ctgtaccggg agaataagcc     420
ccggctaact ccgtgccagc agccgcggta atacggaggg ggctagcgtt gttcggaatt     480
actgggcgta aagcgcacgt aggcggcttt gtaagtcaga ggtgaaagcc tggagctcaa     540
ctccagaact gcctttgaga ctgcatcgct tgaatccagg agaggtgagt ggaattccga     600
gtgtagaggt gaaattcgta gatattcgga agaacaccag tggcgaaggc ggctcactgg     660
actggtattg acgctgaggt gcgaaagcgt ggggagcaaa caggattaga taccctggta     720
gtccacgccg taaacgatga taactagctg tccgggcact tggtgcttgg gtggcgcagc     780
taacgcatta agttatccgc ctggggagta cggccgcaag gttaaaactc aaaggaattg     840
acgggggccc gcacaagcgg tggagcatgt ggtttaattc gaagcaacgc gcagaacctt     900
accagcgttt gacatggtag gacgacttcc agagatggat ttcttcccttt cggggaccta    960 cacacaggtg ctgcatggct gtcgtcagct cgtgtcgtga gatgttgggt taagtcccgc    1020
```

-continued

```
aacgagcgca accctcgact ttagttacca tcattaagtt gggtacttta aagtaaccgc   1080
cggtgataag ccggaggaag gtggggatga cgtcaagtcc tcatggccct tacgcgctgg   1140
gctacacacg tgctacaatg gcaagtacag tgggcagcaa tcccgcgagg gtgagctaat   1200
ctccaaaact tgtctcagtt cggattgttc tctgcaactc gagagcatga aggcggaatc   1260
gctagtaatc gcggatcagc atgccgcggt gaatacgttc ccaggccttg tacacaccgc   1320
ccgtcacacc atgggagttg ggttcacccg aaggcgttgc gctaactcag caatgagagg   1380
caggcgacca cggtgggctt agcgactggg gtgaagtcgt aacaaggtag ccgtagggga   1440
acctgc                                                              1446
```